United States Patent [19]

Laursen

[11] 4,303,471
[45] Dec. 1, 1981

[54] METHOD OF PRODUCING FLUFFED PULP

[75] Inventor: Bente L. Laursen, Ektorp, Sweden

[73] Assignee: Berol Kemi AB, Stenungsund, Sweden

[21] Appl. No.: 59,451

[22] Filed: Jul. 20, 1979

[30] Foreign Application Priority Data

Jul. 21, 1978 [SE]  Sweden ............................. 7808056

[51] Int. Cl.³ .............................................. D21H 3/08
[52] U.S. Cl. .................................. 162/158; 162/179; 252/351; 252/357
[58] Field of Search ............... 162/158, 179; 252/351, 252/357

[56] References Cited

U.S. PATENT DOCUMENTS

| | | | |
|---|---|---|---|
| 3,499,823 | 3/1970 | Croon | 162/158 |
| 3,677,886 | 7/1972 | Forssblad | 162/158 |
| 3,930,933 | 1/1976 | George et al. | 162/158 |

*Primary Examiner*—William F. Smith
*Attorney, Agent, or Firm*—Fred Philpitt

[57] ABSTRACT

The invention relates to a method at the production of absorbent cellulose pulp, so-called fluff. By using certain nonionic fatty acid esters in combination with cationic retention agents, good disintegration properties of the cellulose pulp is obtained and the fluff which is obtained after dry-defibration has fast liquid absorption.

The esters, which are used, are partially fatty acid esters of polyvalent alcohols, and as cationic retention agents quaternary ammonium compounds can e.g. be used.

10 Claims, No Drawings

METHOD OF PRODUCING FLUFFED PULP

TECHNICAL FIELD

The present invention relates to a method of producing cellulose pulp, which by dry-disintegration gives so-called fluff, having good liquid absorption and short absorption times.

BACKGROUND ART

Absorbent cellulose products are produced by dry-defibration of cellulose pulp to form fluff, which is used in e.g. sanitary products, such as diapers and sanitary napkins. For this purpose the cellulose pulp should have a low mechanical strength, in order to make it possible to separate the fibres from each other without destroying them, and in order to reduce the energy, necessary for the disintegration. The fluff, obtained after the dry-disintegration, should have good liquid absorption capacity and short absorption time.

It is known to use cationic surface-active agents, such as quaternary ammonium compounds, for reducing the bonds between the cellulose fibres. These compounds contain one or several long fatty chains, and thus give a considerable impairment of the water absorption time. Further disadvantages of the quaternary ammonium compounds are, that they, as they usually have a chloride ion as anion, give rise to corrosion damages on equipment, and that they often reduce the brightness of the fluff.

It is also known to add nonionic substances to cellulose pulp, in order to reduce the bonding forces. According to the Swedish patent application No. 14914/68, nonionic substances, which are ethoxylated or propoxylated aliphatic alcohols or alkyl phenols, are used, and the Swedish patent application No. 7507270-2 discloses a process, wherein alkoxylated aliphatic alcohols are used in combination with quaternary ammonium compounds as retention agents.

DISCLOSURE OF INVENTION

According to the present invention, it has been found, that an excellent effect with respect to the properties, which are essential for the production of fluff, and for the fluff itself, is obtained by using certain nonionic fatty acid esters in combination with cationic retention agents.

According to the invention, nonionic compounds are used at the production of absorbent cellulose pulp, which compounds consist of partial fatty acid esters of polyvalent alcohols, having 2 to 8 carbon atoms, or anhydrides of these, or polyethylene or polypropylene glycols, having molecular weights of up to 500.

The nonionic compounds themselves have a very low affinity to cellulose fibres, but by employing a cationic compound as a retention agent for the nonionic compounds their positive effect on the disintegration energy and on the liquid absorption time can be developed. The combination of the particular nonionic compound and a cationic retention agent gives the for the production of fluff and the fluff essential combination of properties, i.e. good disintegration properties and short water absorption times.

The obtained satisfactory effect is obtained, when the compounds are used in concentrations, wherein they, each individually, would not give a corresponding effect. Fluff produced according to the invention shows a good brightness and good liquid absorption capacity. The fast liquid absorption remains essentially unchanged on aging.

The nonionic compound, which is used according to the invention, and which is the main fluff chemical, is a partial fatty acid ester of alcohols, as previously defined, and is thus a fatty acid ester, containing at least one free hydroxyl group.

The fatty acid part of the esters consists of a saturated or un-saturated fatty acid, having 8 to 22 carbon atoms, preferably 10 to 18 carbon atoms, and as examples of suitable fatty acids can be mentioned lauric acid, myristic acid, stearic acid, oleic acid and linoleic acid.

Suitable polyvalent alcohols, or anhydrides thereof, for forming esters with the fatty acids, comprise ethylene glycol, glycerol, diglycerol and higher glycerols, propylene glycol, butylene glycol, diethylene glycol, triethylene glycol, xylitol, erytritol, pentaerythritol, sorbitol, sorbitan and polyethylene glycols and polypropylene glycols of molecular weights of up to 500.

Commercially available esters of glycerol and other higher alcohols are generally mixtures of mono- and diesters and higher esters, and they do also differ with respect to the position of the esterified hydroxyl groups. Sorbitan esters and ethoxylated sorbitan esters are also usually mixtures of partial esters of sorbitol and its anhydride. Nonionic compounds, which are mixtures of esters, are, of course, within the scope of the invention. As examples of sorbitan esters, which can be used according to the present invention can be mentioned those, which are commercially available among other names under that of Span ® and the ethoxylated derivatives of the trade name Tween ®.

As examples of suitable fatty acid esters can be mentioned glycerol mono-stearate, glycerol monooleate, sorbitan monolaurate, sorbitan monooleate, diethylene glycol monostearate, diethylene glycol monooleate, propylene glycol monooleate.

The preferred nonionic compounds are the fatty acids of alcohols, containing at least one ether group, such as the fatty acid esters of diethylene glycol, triethylene glycol, polyethylene glycol and polypropylene glycol. Especially preferred are the fatty acid esters of diethylene glycol.

The fatty acid esters are used in combination with cationic retention agents, and of the total amount of added nonionic and cationic compounds, the amount of cationic compounds should be within the range of 2 to 30 percent by weight, preferably within the range of 5 to 15 percent by weight.

At the production of fluffed pulp, the total amount of nonionic and cationic compounds added to the cellulose should be within the range of 0.05 to 2 percent by weight, and preferably within the range of 0.1 to 0.8 percent by weight, based on dry cellulose. The addition can be made to a suspension of cellulose pulp, which is preferred, but it can also be made during the formation of a sheet or web material. The nonionic and cationic compounds can further be added to the aggregates of fibres, which are obtained in some of those processes, which utilize the so-called flash-drying. The cellulose pulp, which has been treated according to the invention is subsequently dry-disintegrated in a manner known per se.

Quaternary ammonium compounds or tertiary amines, containing at least one higher aliphatic hydrocarbon group, i.e. a straight or branched, substituted or unsubstituted alkyl or alkenyl group with 8 to 20 carbon atoms, are used as retention agents. The higher aliphatic hydrocarbon residue is preferably an alkyl group. The retention agents can be used each individually or combined with each other.

Quaternary monoammonium compounds are preferred as retention agents and these compounds can be characterized by the general formula

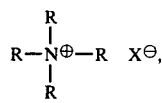

wherein at least one of the groups R is an aliphatic hydrocarbon residue with 8 to 20 carbon atoms, and the other substituents, independent of each other, are alkyl groups, having 1 to 4 carbon atoms, benzyl groups, $(C_2H_4O)_nH$ or $(C_3H_6O)_nH$, whereby n=1-6, preferably n=1. The total number of ethylene oxide or propylene oxide groups in the molecule should, however, not exceed 10. The preferred anion is chloride, but this can, of course, be replaced by any other anion, such as bromide-, ethyl sulphate ion, etc. As examples of suitable quaternary ammonium compounds can be mentioned octyl trimethyl ammonium chloride, dioctyl dimethyl ammonium chloride, decyl trimethyl ammonium bromide, didecyl dimethyl ammonium chloride, didecyl benzyl methyl ammonium chloride, octadecyl trimethylammonium chloride, cetyl trimethyl ammonium bromide.

In the quaternary ammonium compounds of the above formula, the group or the groups, which contain a higher aliphatic hydrocarbon residue, may also be substituted with ethylene oxide groups.

The retention agents can further be tertiary amines, whereby is understood as well tertiary mono- as di- and polyamines. The mono- and diamines are, however, preferred. The amines can be present as free amines or in the form of salts, e.g. in the form of hydrochlorides.

Tertiary monoamines have the general formula $(R)_3N$, wherein at least one group is an aliphatic hydrocarbon residue with 8 to 20 carbon atoms and the other substituents are lower alkyl groups with 1 to 4 carbon atoms or the groups $(C_2H_4O)_nH$ or $(C_3H_6O)_nH$, where n=1-6, preferably n=1. The number of such groups in each molecule should, however, not exceed 10. The higher aliphatic group or groups of the amines can also contain ether bonds. As examples of amines can be mentioned decyl dimethyl amine, didecyl methyl amine, cetyl-di-(2-hydroxyethyl)-amine, alkyl-3-oxypropyl-dimethyl amine.

The di- and polyamines can be characterized by the general formula

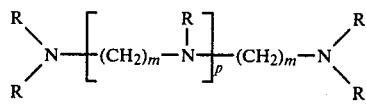

where, in a corresponding manner, the higher aliphatic group or groups may contain ether linkages and the other substituents, independent of each other, are lower alkyl groups or $(C_2H_4O)_nH$ or $(C_3H_6O)_nH$, wherein n=1-6, preferably 1. m is 2 to 6 and P is 0,1 or higher. Some examples of suitable diamines are N-stearyl - N - hydroxyethyl, N'- di(2-hydroxyethyl)- 1,3 propanediamine dihydrochloride, N-decyl-N-hydroxypropyl, N'-di (hydroxypropyl) propanediamine dihydrochloride.

The diamines and polyamines can also be partly or completely quaternized with common quaternizing agents, such as methyl chloride, benzyl chloride and diethyl sulphate.

The invention also relates to a composition for the preparation of absorbent cellulose pulp, which composition consists of a mixture of a partial fatty acid ester of diethylene glycol and a quaternary ammonium compound, containing at least one aliphatic hydrocarbon group, having 8 to 20 carbon atoms, whereby the amount of quaternary ammonium compound is within the range of 2 to 30 percent by weight, based on the mixture, preferably within the range of 5 to 15 percent by weight.

The invention is further illustrated in the following example.

EXAMPLE 1

A mixture of diethylene glycol mono-oleate and didecyl methyl, benzyl ammonium chloride in a weight ratio of 9:1 was added to a suspension of 1% bleached sulphate pulp. The pH of the suspension was 7. Sheets were formed in a laboratory sheet machine in the usual manner. After drying, the sheets were examined with respect to mechanical strength, burst index according to SCAN-P-24:68 and water absorption time. The water absorption time was measured according to a method, where the time is determined for absorption of distilled water in a fluff column of 4.0 grams, which has been compressed to a height of 3.5 cm in a test cylinder, having a diameter of 4.9 cm.

The results are shown in the table below. The defibration energy for the reference was 120 kWh/ton. This was set as 100% and the defibration energy, when using the combination according to the invention, was expressed with respect hereto.

| % added product, based on dry pulp | Water absorption time, sec. | Burst Index | Defibration energy, % |
| --- | --- | --- | --- |
| Reference (no addition) | 8.2 | 27.5 | 100 |
| 0.3 | 9.9 | 16.9 | 68 |
| 0.6 | 10.5 | 10.6 | 51 |

As is evident from the table the invention gave products, having both low mechanical strength and fast water absorption.

EXAMPLE 2

To a suspension of 1% bleached sulphate pulp having a pH of 7 different combinations of nonionic compounds and cationic retention agents according to the invention were added.

The following combinations were tested:
(a) A mixture of monoleate of a polyethylene glycol having a molecular weight of 200 and didodecyl dimethyl ammonium chloride in a weight ratio of 9:1.
(b) A mixture of monooleate of a polyethylene glycol having a molecular weight of 200 and didecyl methylamine in a weight ratio of 9:1.
(c) A mixture of sorbitan monolaurate and didecyl dimethyl ammonium chloride in a weight ratio of 9:1.

(d) A mixture of monolaurate of a polyethylene glycol having a molecular weight of 400 and didecyl dimethyl ammonium chloride in a weight ratio of 9:1.

Sheets were formed in a laboratory sheet machine in the usual manner. After drying, the sheets were examined with respect to mechanical strength, burst index according to SCAN-P-24:68 and water absorption time. The water absorption time was measured according to a method, where the time is determined for absorption of distilled water in a fluff column of 4.0 grams, which has been compressed to a height of 3.5 cm in a test cylinder, having a diameter of 4.9 cm. The easiness with which the produced sheets were de-fiberized was estimated by finger tearing.

The results are shown in the table below.

| Added product, % based on dry pulp | | Water absorption time, sec. | Burst Index | Fiberization |
| --- | --- | --- | --- | --- |
| Reference (no addition) | | 8.4 | 28.6 | not acceptable |
| a | 0.3 | 10.4 | 15.4 | acceptable |
|   | 0.6 | 11.8 | 11.5 | good |
|   | 0.9 | 12.4 | 7.7 | good |
| b | 0.9 | 11.7 | 15.0 | acceptable |
| c | 0.9 | 11.9 | 15.5 | acceptable |
| d | 0.3 | 11.1 | 15.6 | acceptable |
|   | 0.6 | 11.6 | 12.4 | acceptable |
|   | 0.9 | 12.0 | 11.1 | good |

I claim:

1. In the method that includes:
    forming a liquid suspension of cellulose pulp, removing a substantial portion of the liquid to form an essentially dry mass of cellulose pulp, and
    disintegrating the essentially dry mass of cellulose pulp into a fluff,
the improvement which comprises reducing the amount of energy required to disintegrate said mass into fluff which comprises including in said liquid suspension a mixture of
    (a) a non-ionic compound in an amount sufficient to reduce the bonding forces between cellulose fibers, and
    (b) at least one cationic retention agent,
        said nonionic compound being a partial fatty acid ester of polyvalent alcohol having 2-8 carbon atoms, or an anhydride thereof, or a partial fatty acid ester of polyethylene glycol or polypropylene glycol having a molecular weight up to 500.

2. A method according to claim 1 characterized in that the nonionic compound is a fatty acid ester of diethylene glycol.

3. A method according to claim 1 or 2 characterized in that the fatty acid ester is used in combination with a quaternary ammonium compound containing at least one aliphatic hydrocarbon group having 8 to 20 carbon atoms.

4. The method according to claim 3 wherein the amount of the quaternary ammonium compound is 2 to 30 percent by weight of the total weight of said nonionic and cationic compounds.

5. A method according to claim 1 wherein said nonionic compound is selected from the group consisting of diethylene glycol mono-oleate, mono-oleate of polyethylene glycol, having a molecular weight of 200-400 and sorbitan monolaurate and said cationic retention agent is selected from the group consisting of didodecyl dimethyl ammonium chloride, didecylmethylamine, didecyl dimethyl ammonium chloride and didecyl methyl benzyl ammonium chloride.

6. A composition for facilitating the debonding of an aqueous cellulose pulp solution comprising in combination:
    (a) a non-ionic compound in an amount sufficient to reduce the bonding forces between celulose fibers, and
    (b) at least one cationic retention agent,
        said nonionic compound being a partial fatty acid ester of polyvalent alcohol having 2-8 carbon atoms, or an anhydride thereof, or a partial fatty acid ester of polyethylene glycol or polypropylene glycol having a molecular weight up to 500.

7. A composition according to claim 6 characterized in that the nonionic compound is a fatty acid ester of diethylene glycol.

8. A composition according to claim 6 or 7 characterized in that the fatty acid ester is used in combination with a quaternary ammonium compound containing at least one aliphatic hydrocarbon group having 8 to 20 carbon atoms.

9. A composition according to claim 6 wherein the amount of the quaternary ammonium compound is 2 to 30 percent by weight of the total weight of said nonionic and cationic compounds.

10. A composition according to claim 6 wherein said nonionic compound is selected from the group consisting of diethylene glycol mono-oleate, mono-oleate of polyethylene glycol, having a molecular weight of 200-400 and sorbitan monolaurate and said cationic retention agent is selected from the group consisting of didodecyl dimethyl ammonium chloride, didecylmethylamine, didecyl dimethyl ammonium chloride and didecyl methyl benzyl ammonium chloride.

* * * * *